United States Patent [19]
Martin

[11] B 4,013,704
[45] Mar. 22, 1977

[54] 2,5-DIISOPROPYLTEREPHTHALONITRILE

[75] Inventor: Elmore Louis Martin, Wilmington, Del.

[73] Assignee: E. I. Du Pont de Nemours and Company, Wilmington, Del.

[22] Filed: May 2, 1975

[21] Appl. No.: 573,991

[44] Published under the second Trial Voluntary Protest Program on March 30, 1976 as document No. B 573,991.

Related U.S. Application Data

[63] Continuation of Ser. No. 241,850, April 6, 1972, abandoned, which is a continuation-in-part of Ser. No. 153,428, June 15, 1971, abandoned.

[52] U.S. Cl. ............................ 260/465 H; 71/105
[51] Int. Cl.$^2$ ...................................... C07C 121/58
[58] Field of Search .............................. 260/465 H

[56] References Cited
UNITED STATES PATENTS 3,290,353  12/1966  Battershell et al. ............... 260/465

*Primary Examiner*—Lewis Gotts
*Assistant Examiner*—Dolph H. Torrence
*Attorney, Agent, or Firm*—Anthony P. Mentis

[57] ABSTRACT

2,5-Diisopropylterephthalonitrile is a selective herbicide.

1 Claim, No Drawings

2,5-DIISOPROPYLTEREPHTHALONITRILE

CROSS-REFERENCE TO RELATED APPLICATIONS

This is a continuation of my copending application Ser. No. 241,850 filed Apr. 6, 1972, now abandoned, which is a continuation-in-part of my abandoned application Ser. No. 153,428 filed June 15, 1971.

BACKGROUND OF THE INVENTION

This invention relates to 2,5-diisopropylterephthalonitrile, its use as a selective herbicide, and herbicidal compositions containing it as active component.

Belgian Patent 645,904, dated Mar. 31, 1964, discloses halogen-substituted benzonitriles and benzodinitriles. The benzodinitriles (phthalonitriles) are either terephthalonitriles or isophthalonitriles. The patent discloses that the benzonitriles have herbicidal activity, and the benzodinitriles have fungicidal, bactericidal, and nematocidal activity.

Belgian Patent 637,794, dated Sept. 24, 1963, discloses certain hydroxy-, acyloxy-, or alkoxycarbonyloxy-substituted benzonitriles as herbicides.

U.S. Pat. No. 3,027,248, issued Mar. 27, 1962, discloses benzonitriles substituted with one or more halogen, alkyl, and/or nitro groups, and their use as plant growth regulants.

British Patent 755,148 (1956) discloses 2,4-dicyanotert-butylbenzene as an intermediate in a polymer preparation.

German Patent 1,203,424 (1963) discloses benzonitriles substituted with one or more alkoxy, alkyl, nitro, and/or cyano groups, and their use as bactericidal and fungicidal agents.

Japanese Patent Publication 71,42397 discloses certain 4-amino or alkoxy-5-nitroisophthalonitriles as herbicides.

SUMMARY OF THE INVENTION

According to this invention, it has now been discovered that 2,5-diisopropylterephthalonitrile is an excellent selective herbicide.

The invention also includes a method of controlling undesired vegetation for the protection of crops which comprises a preplant soil incorporated, preemergence or postemergence application of a herbicidally effective amount of the compound of the invention.

The compound of the invention exhibits herbicidal activity against one or more of a variety of weeds, including common crabgrass (*Digitaria spp.*), johnsongrass (*Sorghum halepense*), giant foxtail (*Setaria faberi*), dallisgrass (*Paspalum dilitatum*), morningglory (*Ipomoea sp.*), curly dock (*Rumex crispus*), barnyardgrass (*Echinochloa crusgalli*) and pigweed (*Amaranthus sp.*). At the application level at which the novel compound controls undesirable vegetation it is safe for use with valuable crops and can be used with such crops as corn, soybeans, and rice.

The compound should be applied at a rate in the range of about 1—10 kilograms active ingredient per hectare. The optimum rate of application in a given instance will depend upon many factors, including crop, soil type, weed population and method of application. The compound will provide some control of some species when applied postemergence to the weeds, but preemergence application will generally be more effective. For selectively controlling weeds in crops, the compound will be most effective when applied preemrgence to both crop and weeds. In some cases, incorporation of the compound into the soil will improve weed control.

Weeds controlled include crabgrass (*Digitaria spp.*), barnyardgrass (*Echinochloa crusgalli*), junglerice (*Echinochloa colonum*), foxtail (*Setaria spp.*), witchgrass (*Panicum capillare*), goosegrass (*Eleusine indica*), pigweed (*Amaranthus retroflexus*), wild mustard (*Brassica spp.*), curly dock (*Rumex crispus*), johnsongrass (*Sorghum halepense*) from seed, cheat (*Bromus secalinus*), downy brome (*Bromus tectorum*) and blackgrass (*Alopurcurus mysuroides*).

It is sometimes advantageous to combine a compound of this invention with another herbicide in order to increase the spectrum of weeds controlled and to minimize the chances of injury to the current or subsequent crops. The exact combination which may be used to the best advantage will depend upon the crop, the weeds to be controlled and the environment in which the crop is growing, but can be readily selected by one with ordinary skill in the art. The use of other herbicides in combination with the herbicide of this invention will provide control of a wide variety of broadleaved weeds including ragweed (*Ambrosia spp.*) lambsquarter (*Chenopodium album*), morningglory (*Ipomea spp.*) sicklepod (*Cassia obtusifolia*), smartweed (*Polygonum spp.*), flower-of-an-hour (*Hibiscus trionum*), cocklebur (*Xanthium spp.*), and velvetleaf (*Abutilon theophrasti*), as well as grasses.

Preparation of 2,5-Diisopropylterephthalonitrile

A. 1,4-Dibromo-2,5-diisopropylbenzene

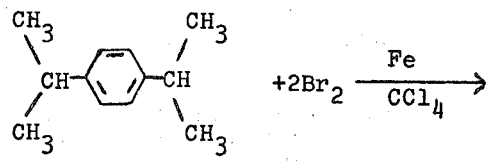

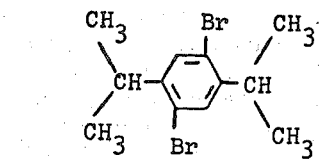

Into a suitable reaction vessel fitted with mechanical stirrer, reflux condenser attached at top to a bubble tube, a thermometer and dropping funnel is charged 162 parts of p-diisopropylbenzene, 200 parts by volume of dry carbon tetrachloride and 2 parts of iron powder (reduced by hydrogen). The reaction mixture is blanketed with nitrogen to exclude moisture; the stirrer is started and the mixture is cooled to −5°C. The bromine solution (340 parts of bromine plus sufficient dry carbon tetrachloride to make 280 parts by volume) is added dropwise during the course of 7 hours (40 parts/hour), the temperature being maintained at −5°C during the addition. Evolved hydrogen bromide is absorbed in a gas absorption trap. The temperature is maintained at −5° to 0°C for 1 hour after the addition of the bromine solution is completed, then the reaction flask is surrounded with an ice bath and allowed to stir overnight. During that time, the ice melts, and the reaction mixture warms to room temperature. The resulting solution is transferred to a separating funnel and shaken vigorously with 100 parts by volume of 6N hydrochloric acid. The organic layer is transferred to a flask, and the carbon tetrachloride is removed at 90°–95°C. To the resulting crude dibromide is added a solution of 50 parts of potassium hydroxide in 300 parts by volume of 95 percent alcohol, and the mixture is refluxed on a steam bath for 1 hour. The resulting solution is poured onto excess ice; the solid is collected and washed with cold water. The moist filter cake is dissolved in ether and the organic layer is separated, washed with 3N hydrochloric acid and treated with decolorizing charcoal and anhydrous magnesium sulfate. The filtrate is concentrated until the internal temperature reaches 50°C; the mixture is cooled in icewater, seeded, and cooled slowly to −40°C. The granular crystals are collected, washed with −70°C ether, and the still moist filter cake is dried at 25°C/10 mm/$P_2O_5$. The yield of crystals melting at 46°–47°C is 232 parts (72 percent). The dibromo compound should be stored in brown bottles.

B. 2,5-Diisopropylterephthalonitrile

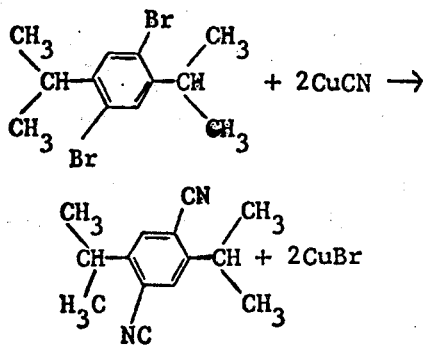

Into a suitable reaction vessel fitted with mechanical stirrer, gas inlet tube, and thermometer is charged 160 parts by volume of N-methylpyrrolidinone distilled under reduced pressure from calcium hydride; the stirrer is started, and 160 parts 1,4-dibromo-2,5-diisopropylbenzene is added, followed by the addition of 104 parts of cuprous cyanide, a slow stream of nitrogen being introduced into the flask. The reaction mixture is well stirred. The reaction mixture goes through a change as the cuprous cyanide partially dissolves and reprecipitates as a granular solid. The temperature is increased to 180°C; the heating mantle is removed; and the temperature is maintained at 180°–185°C. by occasional cooling with warm water. A homogeneous solution is obtained at this temperature. After the exothermic reaction has ceased (3–5 minutes), the temperature is maintained at 185°–195°C. for a reaction period of 1 hour. During this heating period a small amount of a solid may separate. The resulting golden yellow reaction mixture is cooled to 80°C. and poured into a vessel. About 750 parts of crushed ice is added in one portion with stirring; cold water is added to the resulting solid to make a volume of about 1,000 parts; and the mixture is stirred for a few seconds in a Waring blender to break up any large lumps. The reaction mixture is filtered by suction, and the filter cake is washed with about 1,500 parts of cold water.

The moist filter cake is transferred to a vessel, made into a thick slurry with cold water, and transferred to a round bottom flask fitted with a mechanical stirrer, a thermometer and a gas inlet tube extending to nearly the bottom of the flask. Three hundred parts by volume of methylene chloride is added and 52 parts (36 parts by volume at −70°C.) of chlorine (the weight of chlorine should be within ± 1 part) is introduced into the vigorously stirred reaction mixture, the temperature being maintained at 20°–25°C. by means of external cooling and controlling the rate of addition of the chlorine. When about 95 percent of the chlorine has been added, 10 parts by volume of concentrated hydrochloric acid is added and the resulting reaction mixture is stirred for about 5 minutes. The organic layer is separated and the aqueous solution is extracted with 100 parts by volume of methylene chloride. The combined methylene chloride solutions are washed two times with dilute hydrochloric acid, then with a solution of about 25 parts sodium bisulfite in 250 parts of water, treated with decolorizing charcoal and anhydrous magnesium sulfate. The resulting yellow solution is heated to reflux; 10 parts of neutral aluminum oxide is added, and the mixture is refluxed with stirring and filtered through a layer of Celite. The resulting solution is concentrated until crystals begin to separate, then ether is added slowly so as to maintain the volume nearly constant. The concentration is continued until most of the methylene chloride has been replaced by ether and a thick paste of colorless crystals is obtained. The mixture is cooled slowly to −20°C; the crystals are collected and washed with three 75 parts by volume portions of ether at −70°C. and one 75 part by volume portion of pentane at −20°C. After air drying, the crystals are dried at 25°C./10 mm/$P_2O_5$. The yield is 100–102 parts (95 percent), mp 141°–143°C.

The compound of the invention can be formulated for herbicidal use in conventional ways. The formulations can be wettable powders, dusts, suspensions in water and/or organic solvents, solutions, emulsifiables, pellets, highstrength compositions or granules, all as known in the art.

Some herbicidal compositions of this invention are illustrated by the following examples, wherein all the parts, proportions and percentages are by weight unless indicated otherwise.

EXAMPLE A

| | |
|---|---|
| 2,5-diisopropylterephthalonitrile | 80% |
| sodium alkylnaphthalenesulfonate | 2% |
| low viscosity methyl cellulose | 2% |
| diatomaceous earth | 16% |

The ingredients are thoroughly blended, passed through a hammer mill to produce an average particle size under 40 microns, reblended and sifted through a U.S.S. No. 50 sieve (0.2 mm opening) before packaging.

Two kilograms of the above formulation and 1 kilogram of atrazine (Aatrex, 80 W) are mixed with 500 liters of water and applied preemergence to a hectare of sweet corn planted in Sassafras sandy loam soil, in order to control common crabgrass (*Digitaria spp.*), mustard (*Brassica spp.*), giant foxtail (*Setaria faberii*), velvetleaf (*Abutilon theophrasti*), pigweed (*Amaranthus spp.*), and witchgrass (*Panicum capillare*).

EXAMPLE B

| | |
|---|---|
| 2,5-diisopropylterephthalonitrile | 50% |
| 4-chloro-4-ethylamino-6-isopropyl- | |

-continued

| | |
|---|---|
| amino-s-triazine (Atrazine) | 25% |
| attapulgite clay | 22% |
| sodium lignin sulfonate | 2% |
| dioctyl sodium sulfosuccinate | 1% |

The above ingredients are blended, hammer milled to a particle size essentially below 50 microns and reblended.

Four kilograms of the above formulation are dispersed in 450 liters of water with continuous bypass agitation and sprayed uniformly on a hectare of hybrid field corn before the weeds and corn have emerged. The sprayed plot remains free of weeds infesting adjacent unsprayed plots including seedling johnsongrass, crabgrass, goosegrass, foxtail, pigweed and ragweed. The corn grows vigorously and produces a high yield.

EXAMPLE C

| | |
|---|---|
| 2,5-diisopropylterephthalonitrile | 30% |
| 3-(3,4-dichlorophenyl)-1-methoxy-1-methylurea (linuron) | 30% |
| sodium alkylnaphthalenesulfonate | 2% |
| sodium N-methyl-N-oleyl taurate | 3% |
| finely divided synthetic silica | 2% |
| diatomaceous earth | 33% |

The above ingredients are blended, hammer milled to pass a 50-mesh (0.3 mm) screen and reblended.

Carrots planted in Sassafras sandy loam soil are treated preemergence for weed control with the above formulation at 4 kilograms per hectare. The carrots grow vigorously without competition from weeds such as crabgrass, goosegrass, spurge (*Euphorbia spp.*), pigweed, ragweed, lambsquarters and foxtail which are controlled by the treatment. An excellent yield of high-quality carrots is produced.

Superiority of the compound of the invention over two prior art compounds, 5-tert-butylisophthalonitrile and phthalonitrile, is evidenced by the following data.

Seeds of crabgrass (*Digitaria spp.*), sorghum, mustard (*Brassica spp.*), barnyardgrass (*Echinochloa crusgalli*), wild oats (*Avena fatua*), *Cassia tora*, morningglory (*Ipomoea spp.*) radish (*Raphanus spp.*), marigold (*Tagetes spp.*), dock (*Rumex crispus*), bean, corn, soybean, rice, wheat and nutsedge tubers were planted in a growth medium and treated preemergence with the chemicals dissolved in a nonphytotoxic solvent. At the same time cotton having five leaves (including cotyledonary ones), johnsongrass (*Sorghum halepense*) having four leaves, crabgrass and barnyardgrass with three leaves and nutsedge (*Cyperus rotundus*) from tubers with two leaves were treated postemergence. Bush beans with the third trifoliate leaf expanding and sorghum with four leaves were also treated postemergence. Treated plants and controls were maintained in a greenhouse for 16 days, then all species were compared to controls and visually rated for response to treatment.

A qualitative (type of plant response) rating was made as shown in the table below. The letter "C" indicates chlorosis; the letter "B" indicates burn; "G" indicates growth retardation; "E" indicates emergence inhibited; "H" indicates a formative effect (malformation or hormone type); "I" indicates increased chlorophyll; "X" indicates axillary stimulation. A qualitative rating on a scale of 0 to 10 was also made; a rating of zero means no effect; a rating of 10 means maximum effect, e.g. complete kill in case of chlorosis.

The table shows the compound of the invention is several times as effective as the two prior art compounds, for example, against barnyardgrass in the preemergence test; 100 percent effectiveness vs 2 and 0, on a 0 to 10 scale. The superiority of the claimed compound is also borne out by the other data in the table.

POSTEMERGENCE SPECIES

| Lb. Per Acre | COTTON | JOHNSON-GRASS | CRAB-GRASS | BARN-YARD-GRASS | NUT-SEDGE | BEAN | SORGHUM |
|---|---|---|---|---|---|---|---|
| 10 | 1H | 2H | 8G | 5X | | * | |
| 10 | | 3I | 5I | 5I | | | |
| 10 | | | | 7G | | | |
| 02 | 1H | 1H | 8G | | * | | |
| 02 | | | 5I | | | | |
| 0.2 | | | | | | | |
| 1–2 | 0 | 0 | 0 | 0 | 0 | * | * |
| 10 | 0 | 0 | 0 | 0 | 0 | * | * |
| 02 | * | * | * | * | * | 0 | 0 |
| 02 | | | | | | | |
| 10 | 2B | 0 | 0 | 0 | 0 | * | * |
| 02 | * | * | * | * | * | 0 | 0 |
| 02 | | | | | | | |

PREEMERGENCE SPECIES

| Lb. Per Acre | CRAB-GRASS | BARN-YARD-GRASS | SOR-GHUM | WILD OATS | NUT-SEDGE | CASSIA | MORNING-GLORY | MUSTARD |
|---|---|---|---|---|---|---|---|---|
| 10 | 10E | 10E | 10E | 10E | 10E | 8G | 9G | 9C |
| 10 | | | | | | | | |
| 10 | | | | | | | | |
| 02 | 10E | 10E | 10E | 10E | 10E | 6H | 10E | 9C |
| 02 | | | | | | | | |
| 0.2 | | | | | | | | |
| 1–2 | 8G | 10E | 10E | 7G | 0 | 2G | 2G | 2G |
| 10 | 5G | 2G | 2G | 3G | 0 | 2G | 3G | 8C |
| 02 | 0 | 2G | 2G | 0 | 0 | 0 | 0 | 4H |
| 02 | | | | | | | | |
| 10 | 2G | 0 | 5G | 0 | 0 | 0 | 3C | 9C |
| 02 | 0 | 0 | 0 | 0 | 0 | 0 | 0 | 2C |
| 02 | | | | | | | | |

PREEMERGENCE SPECIES
| Lb. Per Acre | RADISH | MARIGOLD | DOCK | BEAN | CORN | SOY-BEAN | RICE | WHEAT | |
|---|---|---|---|---|---|---|---|---|---|
| 10 | 9C | 5G | 10E | 7G | 10C | 9G | 10E | 10E | |
| 10 | | | | | | 5I | | | |
| 10 | | | | | | | | | |
| 02 | 9C | 9E | 10E | 7G | 10C | 1C | 10E | 10E | 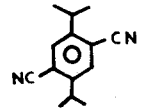 |
| 02 | | | | | | 7G | | | |
| 0.2 | | | | | | | | | 2,5-disopropyl-terephthalonitrile |
| 1–2 | 0 | 0 | 8G | 0 | 2G | 0 | 8H | 8H | |
| 10 | 7G | 3G | 8G | 2G | 3G | 0 | 5G | 5G | |
| 02 | 3G | 0 | 0 | 0 | 0 | 0 | 0 | 3G | 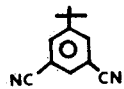 |
| 02 | | | | | | | | | 5-tert-butyliso-phthalonitrile |
| 10 | 9G | 8G | 0 | 1C | 4G | 6G | 3G | 3H | |
| 02 | 0 | 0 | 0 | 0 | 0 | 0 | 0 | 0 | 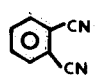 |
| 02 | | | | | | | | | phthalonitrile |
I claim
1. 2,5-Diisopropylterephthalonitrile.
* * * * *